(12) United States Patent
Moavenian

(10) Patent No.: US 10,413,440 B2
(45) Date of Patent: Sep. 17, 2019

(54) SUPPORT FILM

(71) Applicant: WELLAND MEDICAL LIMITED, Crawley, Sussex (GB)

(72) Inventor: Arash Moavenian, Crawley (GB)

(73) Assignee: WELLAND MEDICAL LIMITED, Sussex (GB)

( * ) Notice: Subject to any disclaimer, the term of this patent is extended or adjusted under 35 U.S.C. 154(b) by 618 days.

(21) Appl. No.: 15/026,736

(22) PCT Filed: Oct. 3, 2014

(86) PCT No.: PCT/EP2014/071254
§ 371 (c)(1),
(2) Date: Apr. 1, 2016

(87) PCT Pub. No.: WO2015/052092
PCT Pub. Date: Apr. 16, 2015

(65) Prior Publication Data
US 2016/0235582 A1    Aug. 18, 2016

(30) Foreign Application Priority Data

Oct. 7, 2013 (GB) .................................. 1317667.2
Jul. 22, 2014 (GB) .................................. 1412989.4

(51) Int. Cl.
*A61F 5/443* (2006.01)
*A61F 5/448* (2006.01)

(52) U.S. Cl.
CPC .............. *A61F 5/443* (2013.01); *A61F 5/448* (2013.01)

(58) Field of Classification Search
CPC combination set(s) only.
See application file for complete search history.

(56) References Cited

U.S. PATENT DOCUMENTS

| 793,951 A | * | 7/1905 | Parrish | .................... | F16B 12/60 |
| | | | | | 5/296 |
| 3,878,847 A | * | 4/1975 | Marsan | .................... | A61F 5/445 |
| | | | | | 604/338 |
| 4,610,676 A | * | 9/1986 | Schneider | ............... | A61F 5/448 |
| | | | | | 604/339 |
| 4,610,677 A | * | 9/1986 | Mohiuddin | ............. | A61F 5/448 |
| | | | | | 604/339 |

(Continued)

FOREIGN PATENT DOCUMENTS

| EP | 0793951 A1 | 10/1997 |
| WO | WO 2002/005735 A1 | 1/2002 |
| WO | WO 2004/062537 A1 | 7/2004 |

OTHER PUBLICATIONS

International Search Report and Written Opinion in International Application No. PCT/EP2014/071254), dated Jan. 9, 2015.

*Primary Examiner* — Tatyana Zalukaeva
*Assistant Examiner* — Guy K Townsend
(74) *Attorney, Agent, or Firm* — Potter Anderson and Corroon LLP

(57) ABSTRACT

An ultra-thin highly conformable arc-shaped support film for a flange extender for an ostomy bag comprises a polyurethane film having an adhesive applied to at least one of a body facing surface and an ostomy bag facing surface, wherein the film has a thickness of about 5 pm to about 100 μm and exhibits a high moisture vapor transmission rate even compared to thin films used for film dressings.

24 Claims, 7 Drawing Sheets

(56) References Cited

U.S. PATENT DOCUMENTS

| | | | | |
|---|---|---|---|---|
| 4,681,574 A * | 7/1987 | Eastman | A61F 5/443 | 604/344 |
| 4,701,169 A * | 10/1987 | Steer | A61F 5/443 | 604/344 |
| 5,306,264 A * | 4/1994 | Ferguson | A61F 5/441 | 604/332 |
| 5,496,296 A * | 3/1996 | Holmberg | A61F 5/443 | 604/336 |
| 5,501,677 A * | 3/1996 | Jensen | A61F 5/448 | 604/332 |
| 5,722,965 A * | 3/1998 | Kuczynski | A61F 5/443 | 604/338 |
| 5,730,736 A * | 3/1998 | Sawers | A61F 5/443 | 604/332 |
| 6,293,930 B1 * | 9/2001 | Brunsgaard | A61F 5/443 | 604/322 |
| 6,332,879 B1 * | 12/2001 | Nielsen | A61F 5/448 | 604/344 |
| 6,350,255 B1 * | 2/2002 | von Dyck | A61F 5/441 | 604/332 |
| 9,750,633 B1 * | 9/2017 | Follenius | A61F 5/445 | |
| 2002/0164446 A1 * | 11/2002 | Zhou | A61L 15/58 | 428/40.1 |
| 2003/0060786 A1 * | 3/2003 | Olsen | A61F 5/443 | 604/342 |
| 2005/0010180 A1 * | 1/2005 | Wang | A61F 5/443 | 604/322 |
| 2005/0177119 A1 * | 8/2005 | Tsai | A61F 5/445 | 604/332 |
| 2005/0261646 A1 * | 11/2005 | Conrad | A61F 5/443 | 604/338 |
| 2006/0111683 A1 * | 5/2006 | Leisner | A61F 5/443 | 604/338 |
| 2006/0184145 A1 * | 8/2006 | Ciok | A61F 5/443 | 604/338 |
| 2007/0060855 A1 * | 3/2007 | Leung | A61L 15/225 | 602/41 |
| 2007/0078418 A1 * | 4/2007 | May | A61F 5/443 | 604/336 |
| 2008/0004580 A1 * | 1/2008 | Mullejans | A61F 5/441 | 604/344 |
| 2009/0163883 A1 * | 6/2009 | Christensen | A61F 5/4405 | 604/328 |
| 2009/0247970 A1 * | 10/2009 | Keleny | A61F 5/441 | 604/333 |
| 2010/0168693 A1 * | 7/2010 | Edvardsen | A61F 5/44 | 604/355 |
| 2010/0191204 A1 * | 7/2010 | Bach | A61F 5/443 | 604/344 |
| 2010/0204632 A1 * | 8/2010 | Lykke | A61L 15/58 | 602/54 |
| 2011/0172619 A1 * | 7/2011 | Argent | A61F 5/443 | 604/336 |
| 2011/0230850 A1 * | 9/2011 | Stroebech | A61F 5/443 | 604/344 |
| 2013/0261574 A1 * | 10/2013 | Abrams | A61F 5/4407 | 604/337 |
| 2013/0274696 A1 * | 10/2013 | Lam | A61F 5/443 | 604/332 |
| 2014/0128826 A1 * | 5/2014 | Klein | A61F 5/443 | 604/344 |
| 2014/0316324 A1 * | 10/2014 | Wibaux | C09J 7/385 | 602/56 |
| 2015/0297389 A1 * | 10/2015 | Nyberg | A61F 5/445 | 604/342 |
| 2016/0235582 A1 * | 8/2016 | Moavenian | A61F 5/443 | |
| 2017/0007440 A1 * | 1/2017 | Moavenian | A61F 5/445 | |
| 2018/0085408 A1 * | 3/2018 | Moavenian | A61K 8/65 | |

\* cited by examiner

SUPPORT FILM

The present invention relates to a support film, which can be used to extend the flange of an ostomy bag, thereby increasing security of the connection between a user and the ostomy bag. The support film according to the present invention is especially suitable for medical purposes, in particular the support film can be used in the manufacture of a flange extender for an ostomy bag.

BACKGROUND OF THE INVENTION

Ostomy bags are medical devices that are worn by an individual and they can be used for the collection of waste from a surgically diverted bowel or urinary system of the individual. They are used to collect waste that is output from a stoma created in the ostomate's skin and connected to the intestine or urinary system.

Known ostomy bags comprise a pouch or collection bag manufactured of film and in some cases the pouch is attached mechanically or with adhesive to a flange which forms a mounting plate, commonly referred to as a wafer or a baseplate. In use, the flange is fixed to the skin of an individual and the ostomy bag allows the waste to drain from a stoma into the pouch, while protecting the surrounding skin from contamination by the waste.

Ostomy bags should be air- and water-tight and they should allow the individual to lead an active normal lifestyle that can include all forms of sports and recreation. However, there is a need to make ostomy bags discrete.

The need to provide discrete ostomy bags must be balanced with the need to provide a sufficiently large collection bag so that unexpected deposits can be accommodated by the bag. In addition, the mounting plate must provide a secure attachment to the skin of an ostomate, but it must also be discrete and allow for the ostomy bag to be removed for emptying or disposal. Typically, ostomy bags are emptied at least once per day.

The flange which forms a mounting plate is commonly manufactured of a hydrocolloid which is inherently adhesive and serves to attach the ostomy bag to the skin. Alternatively, it is coated with an adhesive which serves to attach the ostomy bag to the skin.

Secure attachment of the ostomy bag to the skin is of great importance to the user and to the functioning of the product. The level of adhesion, however, varies from product to product and also from person to person, with different skin types and conditions. Loss of, or declines in, adhesion can have potentially difficult and embarrassing consequences for an ostomate, due to the nature of the waste in the pouch and unpredictable output of effluent from the stoma.

In addition to lack of adhesion in some cases, abdominal and peri-stomal irregularities pose another major concern; such irregularities, either as a result of herniation, surgery or anatomical deformity can further increase the risk of pouch detachment due to decreased adhesive contact area and difficulty in application. Thus, ostomates frequently feel that additional security is needed.

Flange extenders for ostomy bags are known. They attempt to address this issue. They are generally arc-shaped, typically manufactured of hydrocolloid, and are placed around the peripheral edge of the flange of an ostomy bag to provide an increased area for adhesion. The typical arc shape is based on the circular or near-circular flange shape itself, around which it is applied.

These known flange extenders, partly overlap the flange and provide additional adhesive support in the area immediately around the flange periphery. This goes some way to address the problem of a secure attachment, but one major disadvantage of currently available flange extenders, predominantly based on hydrocolloid, is that they compromise on comfort for the user. Lack of instant tack or adhesion is another limitation of some of the known flange extenders.

Known flange extenders also suffer from the problem that they lack breathability. In this regard, they suffer from poor moisture transmission rates and this can make them uncomfortable for a user, can reduce wear time and cause skin maceration.

The present invention seeks to provide a support film which addresses one or more of the problems presented by prior art arrangements. In particular, the present invention seeks to provide a support film which addresses major concerns of ostomates in conformability, comfort, security and discreteness.

SUMMARY OF THE INVENTION

Remarkably, it has now been found that an ultra-thin highly conformable support film can be provided that provides a secure attachment, but which is discrete and does not compromise on comfort for the user.

In accordance with the present invention, there is provided an ultra-thin highly conformable support film for use as a flange extender for an ostomy bag wherein the film is selected from a polyurethane film, Polyvinylchloride film, polyester film and vinyl film, and the film has an adhesive applied to at least one of a body facing surface and an ostomy bag facing surface, and the film has a thickness of about 5 μm to about 200 μm.

In one aspect the invention provides a flange extender for an ostomy bag which comprises a film selected from a polyurethane film, polyvinylchloride film, polyester film and vinyl film, wherein the film has an adhesive applied to at least one of a body facing surface and an ostomy bag facing surface, and the film has a thickness of about 5 μm to about 200 μm.

The support film or flange extender of the invention provide the advantage that they provide a tight seal around the flange of an ostomy bag and this prevents leakage of excrement or unpleasant smells, rolling at the edges of the flange or extender, break up during bathing or contact with moisture.

The moisture transmission rate is remarkably high compared to known flange extenders and this makes the support film or flange of the extender of the invention more comfortable for a user to wear for extended periods.

In addition, the thickness of the support film or flange extender of the invention is remarkably thin compared to known flange extenders. This assists with ensuring that the flange extender of the invention does not catch on clothing of a user and this prevents the edges of the support film or flange extender being rolled away from the skin of a user at its edges.

Preferably, the flange extender is arc-shaped or annular. This provides the advantage that one or more flange extenders can be applied to the surface of the skin and the flange of an ostomy bag can be applied to the flange extender(s).

Preferably, the film is polyurethane film.

Preferably, the film has a thickness of about 5 μm to about 100 μm, more preferably, the film has a thickness of about 5 μm to about 50 μm, even more preferably the film has a thickness of about 5 μm to about 10 μm, most preferably the film has a thickness of about 7 μm.

Advantageously, it has been found that a support film according to the invention exhibits high levels of extensibility and is highly breathable. These advantages provide increased comfort for a user.

Preferably, the moisture vapour transmission rate (MVTR) value of the film is in the range of about 500 g/m2/24 h to about 5000 g/m2/24 h. More preferably, it is at least (equal to or greater than) 2000 g/m2/24 h. For example, in an embodiment it is 2444.1 g/m2/24 h.

Preferably, the flange extender can be produced in a multitude of geometries and dimensions to meet the needs for its intended application within ostomy and may also be tailored to a particular pouch or flange style.

Preferably, the film is transparent or translucent. This provides the advantage that in use the skin where the flange extender is placed can be inspected. In addition, it provides the advantage of maximum discretion for a user.

Preferably, the adhesive is acrylic based or silicone-based or PU-based. More preferably, the adhesive is acrylic based.

Preferably, the adhesive has a thickness of about 0.2 μm to about 2 μm, more preferably, the adhesive has a thickness of about 0.8 μm to about 1.2 μm, even more preferably the adhesive has a thickness of about 1 μm.

Preferably, a support film or flange extender according to this aspect of the invention comprises no other features or materials. Alternatively, a support film or flange extender of the invention comprises additional features or materials.

Preferably, the support film or flange extender further comprises at least one release liner (also referred to as an easy-release liner). More preferably, the support film or flange extender has a first release liner which covers the adhesive until the flange extender is applied and a second release liner which acts as a carrier. Just before use, the easy release liner can be peeled away to expose the adhesive. This provides the advantage of protecting the adhesive until it is ready for use. The release liner(s) are preferably divided into a number of sections by perforations or slits, separating the liner into two, or three or more sections. In one embodiment, first and second sections of a release liner are separated by a third section of the release liner. Advantageously, the third section of the release liner may be removed exposing adhesive, while the first and second sections of the release liner remain in position thereby covering opposing ends of the support film. The first and second sections of the release liner can be removed after the exposed adhesive, revealed by removal of the third section of release liner, is attached to the skin and/or flange. This facilitates easier application of the support film or flange extender.

Preferably, a tab is provided for easily removing the release liner(s). This provides the advantage that the tab can be easily gripped and facilitates removal of the easy-release liner to expose the adhesive or film.

Preferably, prior to use, the tab is located between the adhesive and the release liner and extends at least about 5 mm outwardly from the support film or flange extender and the release liner.

Preferably, one or more tabs are provided. Even more preferably, at least two tabs are provided. An arc shaped support film or flange extender described herein preferably has a tab at each opposing end of the arc. This provides the advantage of providing a surface for easy gripping and removal of the release liner prior to use.

Preferably, adhesive is applied to the body facing surface of the film.

Preferably, at least one easy release liner covers the adhesive on the body facing surface of the film or both the body facing surface and an ostomy bag facing surface of the film until the flange extender is ready for use. Just before use, the easy release liner can be peeled away from the body facing surface or both the body facing surface and an ostomy bag facing surface of the film to expose the adhesive. This provides the advantage of protecting the adhesive until it is ready for use.

Preferably, the support film is used to provide a flange extender which is incorporated within the flange design of an ostomy bag and is integral with the ostomy bag. In this embodiment, the flange extender is applied to the flange of an ostomy bag and in use, a user is simply required to apply the flange extender to the skin.

In one embodiment, the support film is attached to a flange of an ostomy bag and extends outwardly therefrom to provide an extension to the flange. This support film may also be incorporated as part of a flange or pouch system whereby the film is attached to the underside of the flange (flange backing) and can open out to form an adhesive extension. This provides the advantage of allowing a smaller hydrocolloid flange to be used, making the product lighter, more comfortable and potentially more secure. In addition, it allows the use of a smaller flange size because the adhesive area is extended by unfolding a thin film.

Alternatively, the flange extender may be provided separately for use with an ostomy bag. In this embodiment, in use, a user is required to apply the flange extender to the skin and the flange of an ostomy bag. This can be achieved by applying the flange extender to the skin of an ostomate first followed by attachment of the flange extender to the flange of an ostomy bag. Alternatively, the flange extender is attached to the flange of an ostomy bag followed by attachment of the flange extender to the skin of an ostomate.

Preferably, the support film of the invention is used to provide a flange extender which has a larger width than currently available flange extenders. (Despite the additional width, the flange extender does not compromise on conformability or comfort for a user). In this regard, the width of a flange extender according to the invention is preferably about 20 mm to about 50 mm. Preferably, the width of a flange extender according to the invention is about 35 mm to about 45 mm. More preferably, the width of a flange extender according to the invention is about 45 mm. This provides the advantage of an increased area for adhesion and this provides added security.

Consequently, the invention provides a package comprising a sachet inside of which is sealed a flange extender according to the invention. Preferably, the package comprises a moulded or vacuum formed base of plastics material in which the flange extenders are provided. Preferably, the sachet contains one or more flange extenders. More preferably, the sachet contains about ten to thirty flange extenders according to the invention.

In another aspect, the invention provides a method for the production of a flange extender described herein, wherein the method comprises providing a film selected from a polyurethane film, polyvinylchloride film, polyester film and vinyl film, wherein the film has a thickness of about 5 μm to about 200 μm, cutting the film to size, applying adhesive to the film, applying an easy release liner to the adhesive.

Preferably, the film is polyurethane film. Preferably, the film is transparent or translucent.

Preferably, the film has a thickness of about 5 μm to about 100 μm, more preferably, the film has a thickness of about 5 μm to about 50 μm, even more preferably the film has a thickness of about 5 μm to about 10 μm, most preferably the film has a thickness of about 7 μm.

Preferably, the adhesive is acrylic based or silicone-based or PU-based. More preferably, the adhesive is acrylic based.

Preferably, adhesive is applied to the body facing surface of the polyurethane film. More preferably, adhesive is applied to both the body facing surface and an ostomy bag facing surface of the polyurethane film.

BRIEF DESCRIPTION OF THE DRAWINGS

The invention will now be described by way of example with reference to the accompanying drawings, in which:—

DETAILED DESCRIPTION OF THE INVENTION

Figure 1:
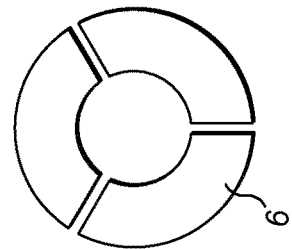
FIG. 1 shows a support film according to the invention. In the drawing the parts are identified by letters as follows: A: Flange, B: Stoma hole, D: Support film, E: two-piece arc support and F: three piece arc support.
Figure 1:
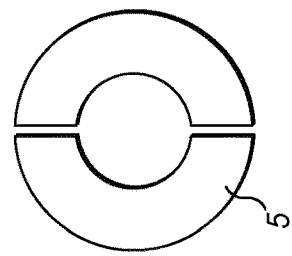
Figure 1:
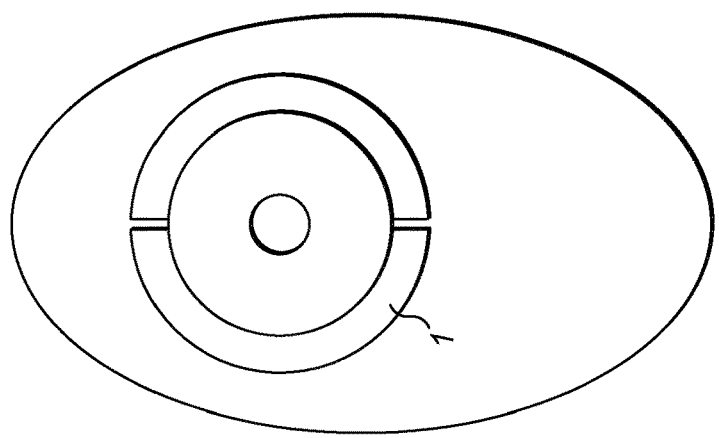
Figure 1:
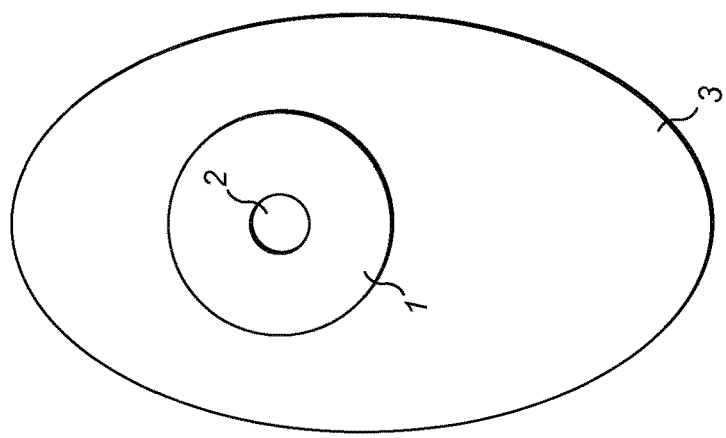
Figure 2:
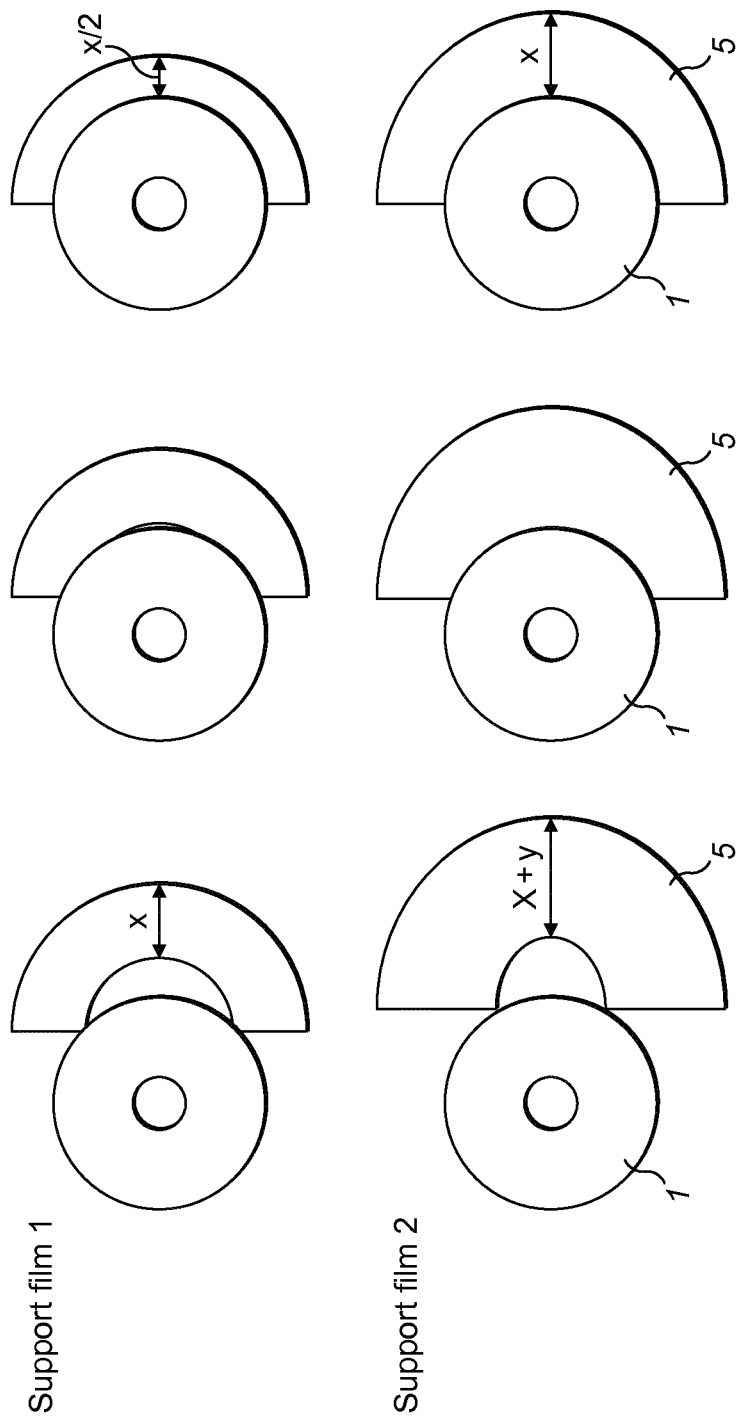
FIG. 2 shows a support film according to the invention similar in size to current flange extenders. Alternative support film 2 has twice the width of support film 1 and provides the entire width of support film 1 for adhesion with skin.

It will be appreciated that aspects, embodiments and preferred features of the invention have been described herein in a way that allows the specification to be written in a clear and concise way. However, it will be appreciated that the scope of the invention may include embodiments having combinations of all or some of the features described. Unless circumstances clearly dictate otherwise, aspects, embodiments and preferred features can be variously combined or separated in accordance with the invention. In a preferred embodiment, a device in accordance with the invention comprises all aspects of the invention.

The word "about" is taken to mean optionally plus or minus 20%, more preferably optionally plus or minus 10%, even more preferably optionally plus or minus 5%, even more preferably optionally plus or minus 2.5%, most preferably optionally plus or minus 1%.

Within the context of this specification the word "comprises" is taken to mean "includes, among other things". It is not intended to be construed as "consists of only".

Within the context of this specification, the word "substantially" means preferably at least 90%, more preferably 95%, even more preferably 98%, most preferably 99%.

Details of flange extenders according to the invention for use with ostomy bags are shown in FIGS. 1 to 3 and 7 to 9.

The ostomy bags have a flange (1), a stoma hole (2) and a pouch (3).

The flange extenders (4) (5) or (6) are manufactured of translucent polyurethane film (10) having a thickness of about 5 μm to about 10 μm. They adhere to the skin of an ostomate and to the flange (1) of an ostomy bag. Acrylic based adhesive (7) is applied to the body facing surfaces of the flange extenders (4) (5) or (6) and an easy release liner (8) covers the adhesive (7). The easy release liner (8) can be peeled away prior to use to expose the adhesive (7). This provides the advantage of protecting the adhesive (7) until it is ready for use.

Figure 8:
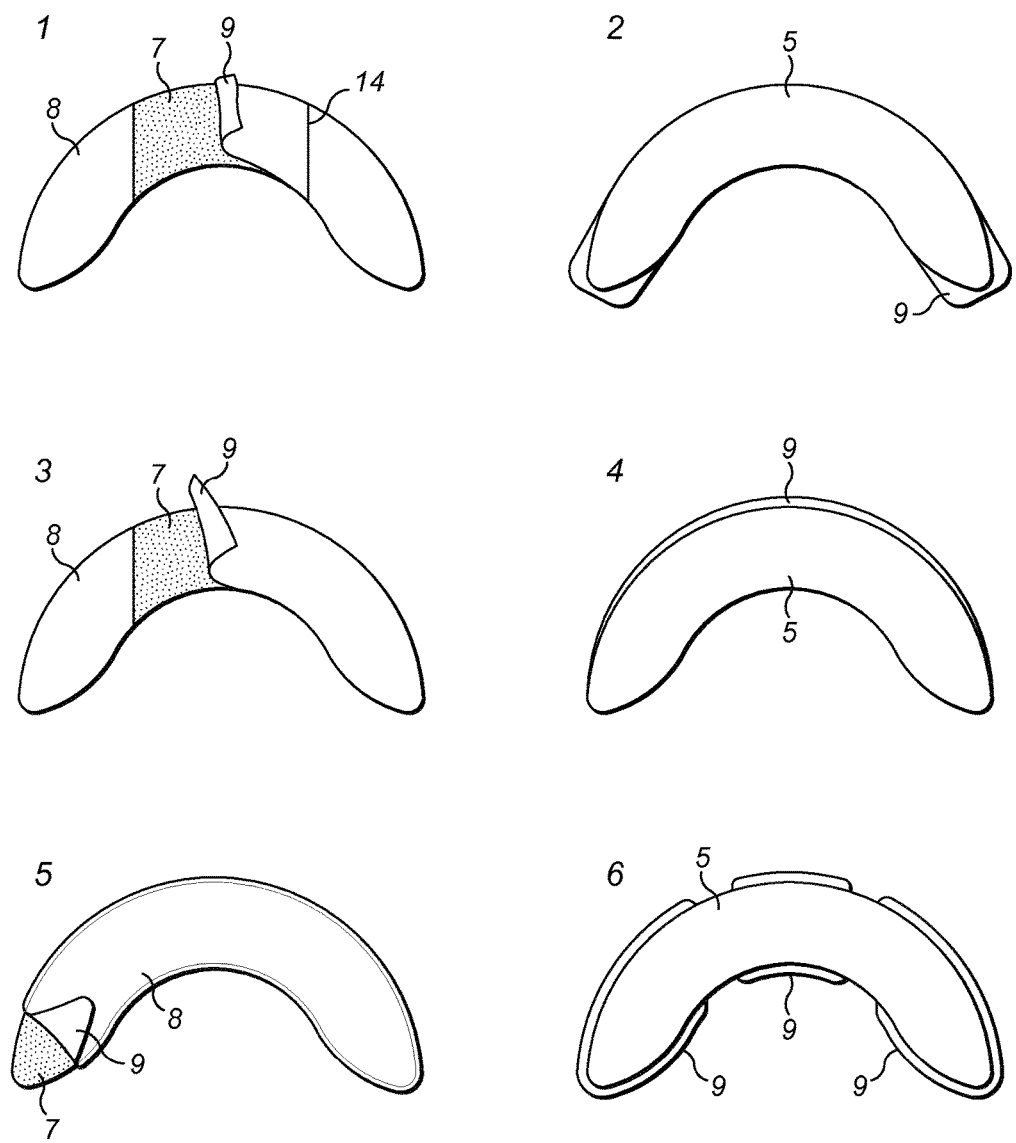
FIG. 8 shows schematics illustrating various release liner designs.

The easy release liner (8) comprises a tab (9) which does not adhere to the adhesive (7). This provides the advantage that the tab (9) can be easily gripped and facilitates removal of the easy-release liner (8) to expose the adhesive (7). Various release liners (8) falling within the scope of the invention are shown in FIGS. 3 and 8.

Figure 3:
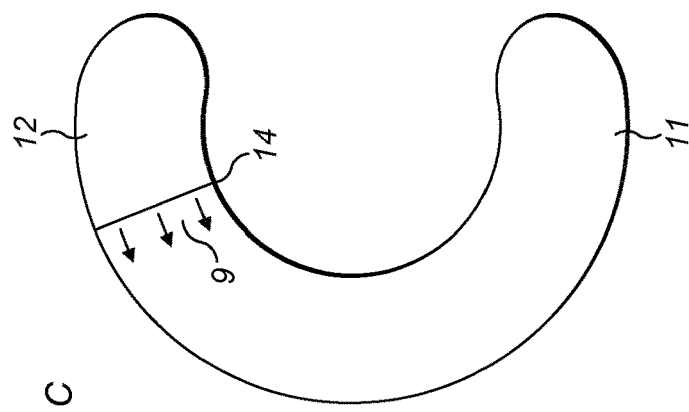
FIG. 3 shows a support film according to the invention, illustrating sections of release liners divided by perforations/slits on the adhesive surface (A) and the release liner on the non-adhesive flange facing side of a support film ((A) and (B)). Two alternatives (A) and (B) are shown wherein the release liners can be removed by pealing outwardly from a line distal to the ends of the film and a further alternative (C) is shown wherein the release liner can be removed by pealing from a line adjacent to an end of the release liner.
Figure 3:
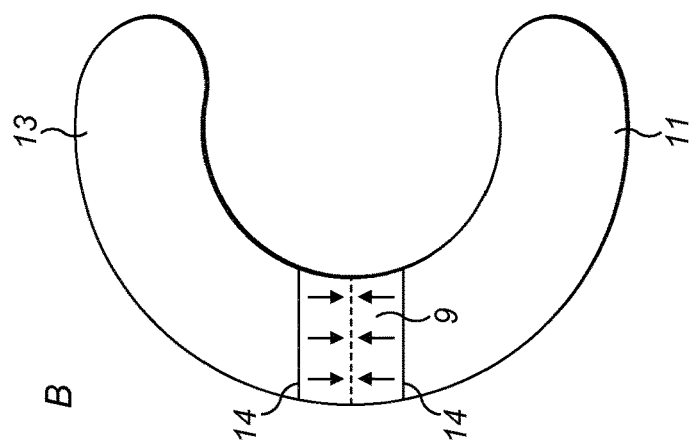
Figure 3:
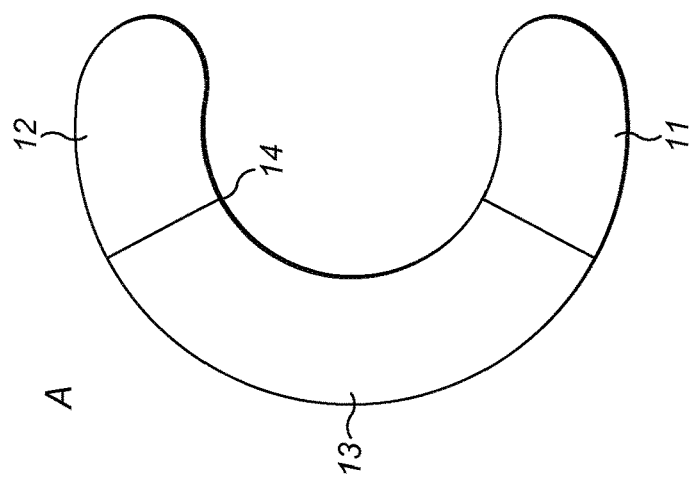

As shown in FIG. 3, the release liner (8) is divided into sections (11), (12) and (13) by perforations or slits (14). First and second sections (11), (13) of a release liner (8) are separated by a third second (12) of the release liner (8). Advantageously, the third section (12) of the release liner (8) may be removed exposing adhesive (7), while the first and second sections (11), (13) of the release liner (8) remain in position thereby covering opposing ends of the flange extender (5). The first and second sections (11), (12) of the release liner can be removed after the exposed adhesive (7) is attached to the skin and/or flange. This facilitates easier application of the support film (10) or flange extender (5).

The moisture vapour transmission rate (MVTR) value of the film (10) is 2444.1 g/m2/24 h.

Figure 7:
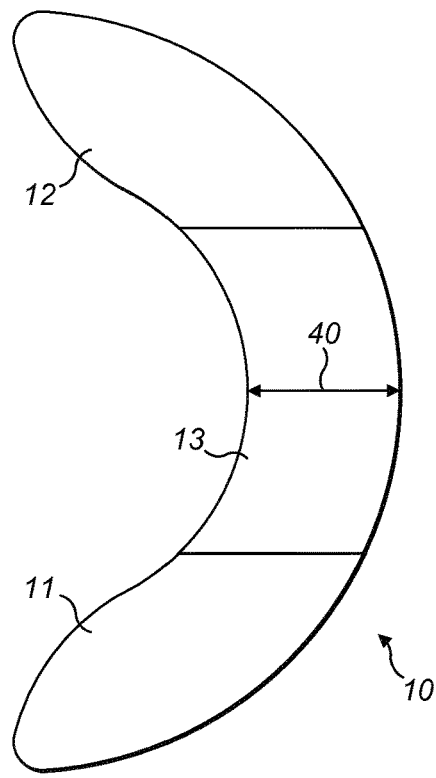
FIG. 7 shows an arc-shaped support film according to the invention. All dimensions are shown in millimeters.

The film (10) can be produced in a multitude of geometries and dimensions to meet the needs for its intended application within ostomy and may also be tailored to a particular pouch (3) or flange (1) style. A possible flange extender (4) (5) or (6) is shown in FIG. 7. It has a width of about 45 mm.

Figure 9:
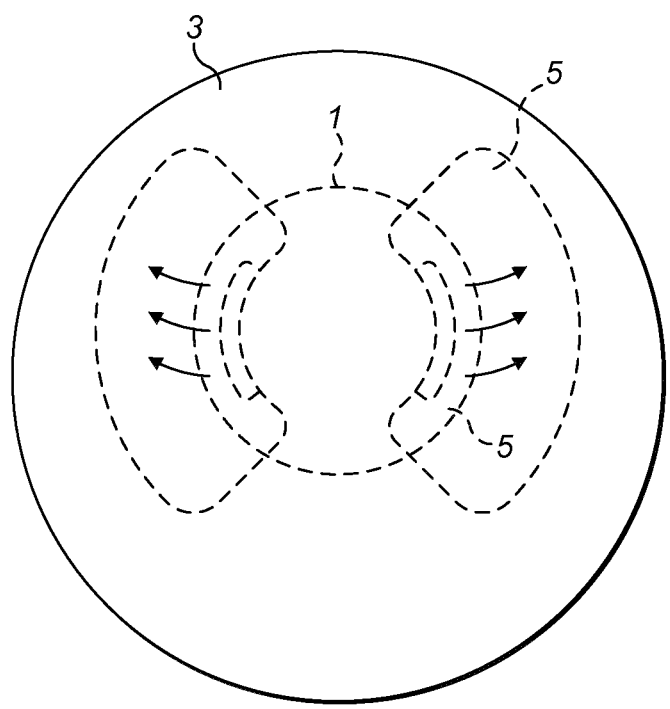
FIG. 9 shows how a support film of the invention forms part of a flange system for an ostomy bag. In this regard, the support film is capable of being folded out to form an extension to the flange.

In one embodiment illustrated in FIG. 9, the flange extender (4) (5) or (6) is incorporated within the flange (1) design of an ostomy bag and is integral with the ostomy bag. In this embodiment, the flange extender (4) (5) or (6) is applied to the flange (1) of an ostomy bag and in use, a user is simply required to apply the flange extender (4) (5) or (6) to the skin.

Alternatively, the flange extender (4) (5) or (6) may be provided separately for use with an ostomy bag. In this embodiment, in use, a user is required to apply the flange extender (4) (5) or (6) to the skin and the flange (1) of an ostomy bag. This can be achieved by applying the flange extender (4) (5) or (6) to the skin of an ostomate first followed by attachment of the flange extender (4) (5) or (6) to the flange (1) of an ostomy bag. Alternatively, the flange extender (4) (5) or (6) is attached to the flange (1) of an ostomy bag followed by attachment of the flange extender (4) (5) or (6) to the skin of an ostomate.

In one embodiment, the flange extender (4) (5) or (6) is sealed in a sachet prior to use. The sachet contains two or three flange extenders.

To manufacture a flange extender (4) (5) or (6), a polyurethane film (10) is provided and cut to size. Acrylic adhesive (7) is applied to the film (10) and applying an easy release liner (8) having a tab (9) for easy removal of the release liner is applied to the adhesive (7).

Figure 4:
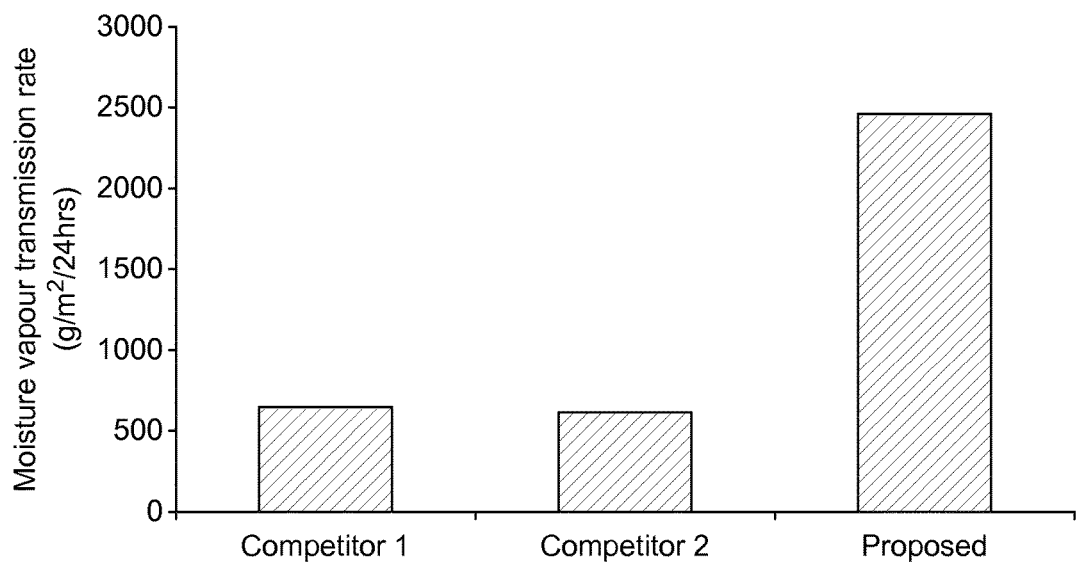
FIG. 4 shows the results of comparative tests of moisture vapour transmission rates (g/m2/24 h) of proposed material against other commercially available leading PU-based films.

FIG. 4 shows the results of moisture vapour permeability tests comparing a flange extender (4) (5) or (6) of the invention with other commercially available films.

This graph compares mean moisture vapour loss of a flange extender film (10) according to the invention against other known PU films used as wound dressings. This comparison is therefore against similar materials but not against hydrocolloid which other flange extenders are actually based on.

The moisture vapour transmission properties were determined in accordance with the European Standard BS EN 13726:2:2002.

For testing to BS EN 13726-2 Section 3.2, In Contact with Water Vapour, five Paddington cups were assembled. 30 ml of de-ionised water was added to each cup which ensured a 5±1 mm air gap at the top of the cup. The test dressings were then applied to the Paddington cups ensuring that the fluid did not come into contact with the dressing. The cups were then weighed to the nearest 0.0001 g using a calibrated analytical balance, then placed in a temperature and humidity controlled incubator used to maintain an environment of 37° C.±2° C. and a relative humidity level below 20% for a period of 24 hours. At the end of the test the cups were removed from the incubator, and immediately reweighed to the nearest 0.0001 g using an analytical balance. From these weighings the loss in weight due to the passage of moisture vapour through the dressing was calculated.

It can be seen that the flange extender of the invention has remarkably superior moisture vapour permeability.

Figure 5:
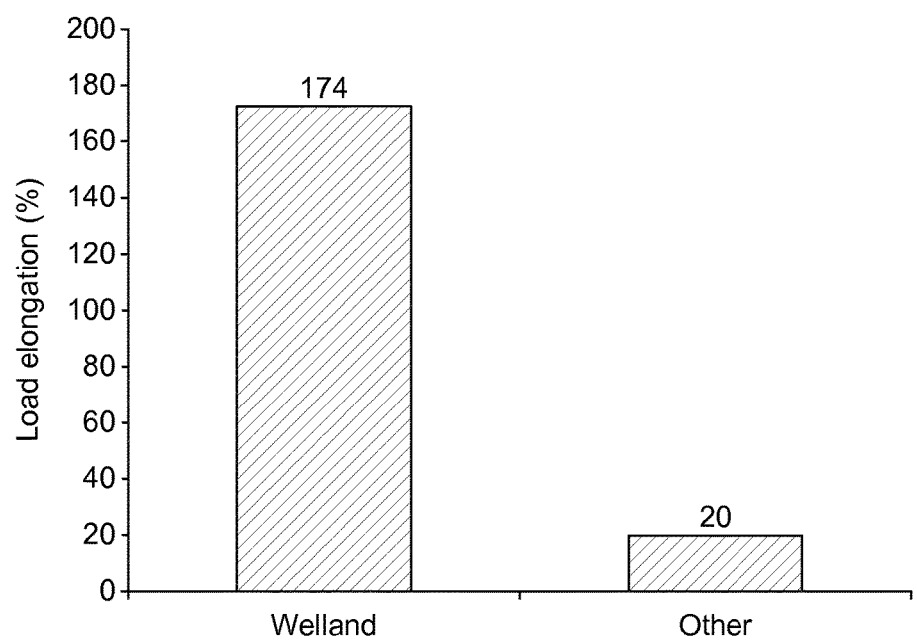
FIG. 5 shows the results of comparative testing of load elongation (%) properties of a support film according to the invention against other commercially available PU-based films

FIG. 5 shows the results of a comparative test of load elongation. In this regard, it can be seen that a flange extender (4) (5) or (6) according to the invention had remarkably superior load elongation. This indicates that a flange extender (4) (5) or (6) according to the invention is likely to have superior comfort compared to flange extenders outside the scope of the invention.

Figure 6:
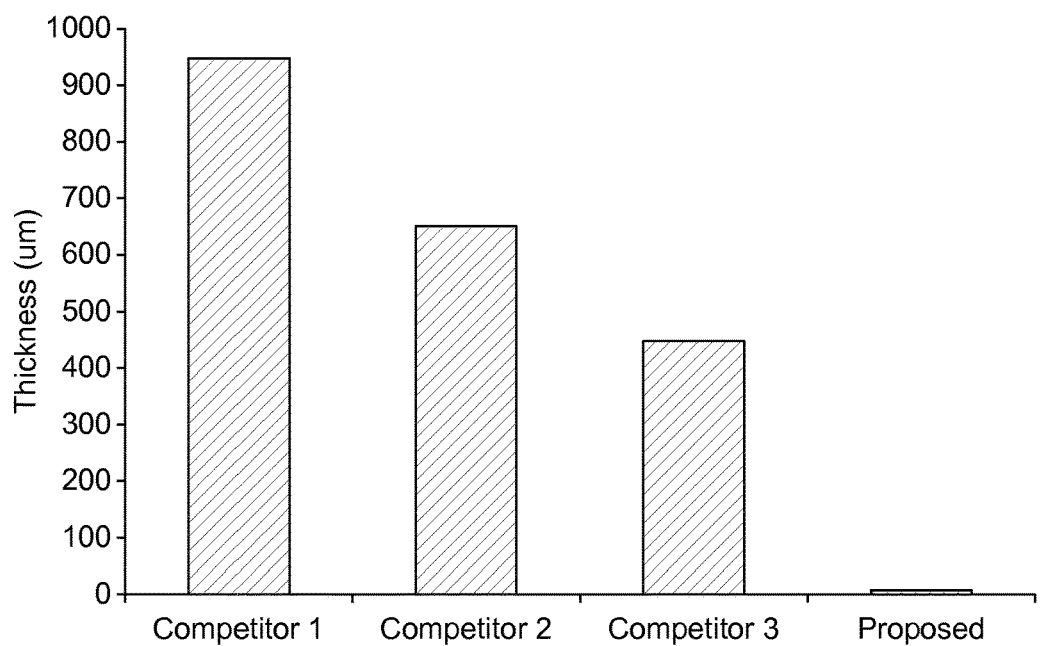
FIG. 6 shows the results of comparative testing showing the thickness of a support film according to the invention against other commercially available flange extenders.

FIG. 6 shows the results of a comparative test of thickness of known flange extenders and the thickness of a flange extender (4) (5) or (6) according to the invention. In this regard, it can be seen that a flange extender (4) (5) or (6) according to the invention had a thickness of 7 μm. In stark contrast, other commercially available flange extenders have greater thickness. Known flange extenders were manufactured of hydrocolloid or PU foam and thickness was measured by the inventors.

The above described embodiments have been given by way of example only, and the skilled reader will naturally appreciate that many variations could be made thereto without departing from the scope of the claims.

The invention claimed is:

1. A flange extender configured for use with a flange of, or with, an ostomy bag, the flange extender comprising:
   a support film; and
   an adhesive applied to at least one surface of the support film;
   wherein the support film comprises a film selected from a polyurethane (PU) film, a polyvinylchloride film, a polyester film, and a vinyl film;
   wherein the adhesive has a thickness of 0.2 μm to 2 μm;
   wherein the at least one surface comprises at least one of a body facing surface, and an ostomy bag facing surface, of the support film; and
   wherein the support film has a thickness of about 5 μm to about 200 μm.

2. A flange extender according to claim 1, wherein the flange extender has a shape that is annular or defines an arc.

3. A flange extender according to claim 1, wherein the support film is polyurethane (PU) film.

4. A flange extender according to claim 1, wherein the support film has a thickness of about 5 μm to about 100 μm.

5. A flange extender according to claim 4, wherein the support film has a thickness of about 5 μm to about 50 μm.

6. A flange extender according to claim 5, wherein the support film has a thickness of about 5 μm to about 10 μm.

7. A flange extender according to claim 6, wherein the support film has a thickness of about 7 μm.

8. A flange extender according to claim 1, wherein the moisture vapour transmission rate (MVTR) value of the support film is in the range of about 500 g/m2/24 h to about 5000 g/m2/24 h.

9. A flange extender according to claim 1, wherein the support film is transparent or translucent.

10. A flange extender according to claim 1, wherein adhesive is provided on the body facing surface of the support film.

11. A flange extender according to claim 1, wherein the adhesive is acrylic-based, silicone-based, or PU-based.

12. A flange extender according to claim 1, wherein the adhesive has a thickness of about 0.8 μm to about 1.2 μm.

13. A flange extender according to claim 12, wherein the adhesive has a thickness of about 1 μm.

14. A flange extender according to claim 1, wherein the flange extender further comprises at least one release liner which:
   covers an outer surface of the adhesive; and is configured to be removable from the support film or flange extender.

15. A flange extender according to claim 14, wherein the flange extender further comprises at least one tab configured for removal of the release liner.

16. A flange extender according to claim 15, wherein the at least one tab is located between the adhesive and the release liner and extends at least about 5 mm outwardly from an outer edge of the adhesive, the support film, and/or the release liner.

17. A flange extender according to claim 15, wherein the at least one tab comprises at least two tabs.

18. A flange extender according to claim 17, wherein the support film has a shape that defines an arc and a tab of the at least two tabs is provided at each opposing end of the arc.

19. A flange extender according to claim 1, wherein the support film is configured to be made integral with, or connected to: the flange of the ostomy bag; and/or the ostomy bag.

20. A flange extender according to claim 1, wherein the support film is configured to: be attached to the flange of the ostomy bag; and to extend outwardly from the flange to provide an extension to the flange.

21. A flange extender according to claim 1, wherein the flange extender is configured to be provided separately from the ostomy bag.

22. A flange extender according to claim 1, wherein the width of the flange extender is about 20 mm to about 50 mm.

23. A flange extender according to claim 1, wherein the flange extender is configured to be sealed in a sachet prior to use.

24. A method for production of a flange extender configured for use with a flange of, or with, an ostomy bag, the flange extender comprising a support film, an adhesive, and a release liner; wherein the method comprises:
  providing the support film comprising a film selected from a polyurethane film, a polyvinylchloride film, a polyester film, and a vinyl film, wherein the support film has a thickness of about 5 µm to about 200 µm;
  providing the adhesive;
  cutting the support film to a size configured for use with the flange of, or with, the ostomy bag;
  applying the adhesive to at least one of: a body facing surface; or an ostomy bag facing surface; of the support film; wherein the adhesive as applied to the support film has a thickness of 0.2 µm to 2 µm; and
  applying a release liner to an outer surface of the adhesive.

* * * * *